(12) United States Patent
Rebergue et al.

(10) Patent No.: US 9,662,439 B2
(45) Date of Patent: May 30, 2017

(54) CONTROLLER FOR THE AUTOMATIC CONTROL OF AN INJECTION DEVICE

(71) Applicant: MEDEX, Saint-Priest (FR)

(72) Inventors: Habib Rebergue, Lyons (FR); Adriana Murillo, Bron (FR); Ali Dghoughi, Grenoble (FR)

(73) Assignee: Medex (FR)

( * ) Notice: Subject to any disclaimer, the term of this patent is extended or adjusted under 35 U.S.C. 154(b) by 79 days.

(21) Appl. No.: 14/406,681

(22) PCT Filed: Jun. 13, 2013

(86) PCT No.: PCT/EP2013/062215
§ 371 (c)(1),
(2) Date: Dec. 9, 2014

(87) PCT Pub. No.: WO2013/186290
PCT Pub. Date: Dec. 19, 2013

(65) Prior Publication Data
US 2015/0151040 A1    Jun. 4, 2015

Related U.S. Application Data

(60) Provisional application No. 61/659,330, filed on Jun. 13, 2012.

(30) Foreign Application Priority Data

Jun. 13, 2012   (FR) ..................... 12 55531

(51) Int. Cl.
*A61M 37/00*    (2006.01)
*A61M 5/148*    (2006.01)
(Continued)

(52) U.S. Cl.
CPC ............ *A61M 5/148* (2013.01); *A61M 5/007* (2013.01); *A61M 5/16831* (2013.01); *A61M 5/172* (2013.01); *A61M 2005/14208* (2013.01)

(58) Field of Classification Search
CPC ........ A61M 2005/14208; A61M 5/007; A61M 5/148; A61M 5/16831; A61M 5/172; A61M 37/00
(Continued)

(56) References Cited

U.S. PATENT DOCUMENTS 3,895,741 A    7/1975 Nugent
5,348,539 A    9/1994 Herskowitz
(Continued)

FOREIGN PATENT DOCUMENTS

EP    0648513 A1    4/1995
EP    0676214 A1    10/1995
(Continued)

OTHER PUBLICATIONS

French Preliminary Search Report, dated Feb. 27, 2013, for French Application No. 1255531.
(Continued)

*Primary Examiner* — Kevin C Sirmons
*Assistant Examiner* — Deanna K Hall
(74) *Attorney, Agent, or Firm* — Marsh Fischmann & Breyfogle LLP (57) ABSTRACT

The invention concerns an device for injecting a patient with a liquid product contained in a container (4), the system comprising a pressurizing unit for driving the liquid product contained in the container, the system further comprising a calculator for estimating the injection flow rate at the outlet of the container, said injection flow rate at the outlet being estimated on the basis of a law of deformation of the system under the effect of the pressure inside the container.

20 Claims, 7 Drawing Sheets

(51) Int. Cl.
  *A61M 5/168* (2006.01)
  *A61M 5/172* (2006.01)
  *A61M 5/00* (2006.01)
  *A61M 5/142* (2006.01)

(58) Field of Classification Search
  USPC .......................................................... 604/133
  See application file for complete search history.

(56) References Cited

U.S. PATENT DOCUMENTS

| | | | |
|---|---|---|---|
| 5,368,569 A | | 11/1994 | Sanese |
| 5,738,657 A | | 4/1998 | Bryant et al. |
| 5,840,026 A | * | 11/1998 | Uber, III .................. A61B 8/06 |
| | | | 128/DIG. 12 |
| 5,997,501 A | | 12/1999 | Gross et al. |
| 6,355,024 B1 | | 3/2002 | Small et al. |
| 7,031,602 B2 | | 4/2006 | Faries, Jr. et al. |
| 8,579,859 B2 | | 11/2013 | Kramer et al. |
| 8,954,354 B2 | | 2/2015 | Ross |
| 9,345,830 B2 | * | 5/2016 | Miller ............... A61M 5/16859 |
| 2011/0318198 A1 | | 12/2011 | Johnson et al. |
| 2013/0211373 A1 | | 8/2013 | Lee |
| 2015/0174315 A1 | | 6/2015 | Rebergue et al. |
| 2015/0224248 A1 | | 8/2015 | Terrasse et al. |

FOREIGN PATENT DOCUMENTS

| | | |
|---|---|---|
| EP | 1382226 B1 | 11/2005 |
| EP | 1788498 A1 | 5/2007 |
| KR | 10-2011-0123081 A | 11/2011 |
| WO | 93/23096 | 11/1993 |
| WO | 93/25269 | 12/1993 |
| WO | WO 97/45150 A1 | 12/1997 |
| WO | 01/023277 | 4/2001 |
| WO | 03/039433 | 5/2003 |
| WO | 2005/072666 | 8/2005 |
| WO | 2006/044409 | 4/2006 |
| WO | 2008/099876 A1 | 8/2008 |
| WO | 2008/137375 | 11/2008 |
| WO | 2012/071307 | 5/2012 |
| WO | WO 2012/176170 A1 | 12/2012 |

OTHER PUBLICATIONS

International Search Report and Written Opinion of the International Searching Authority (Forms PCT/ISA/210 and PCT/ISA/237), dated Oct. 25, 2013, for International Application No. PCT/EP2013/062215.

* cited by examiner

CONTROLLER FOR THE AUTOMATIC CONTROL OF AN INJECTION DEVICE

CROSS REFERENCE TO RELATED APPLICATIONS

This application is the National Phase of PCT International Application No. PCT/EP2013/062215, filed on Jun. 13, 2013, which claims priority under 35 U.S.C. 119(e) to U.S. Provisional Application No. 61/659,330, filed on Jun. 13, 2012 and under 35 U.S.C. 119(a) to Patent Application No. 1255531, filed in France on Jun. 13, 2012, all of which are hereby expressly incorporated by reference into the present application.

TECHNICAL FIELD

The present invention concerns the general technical field of contrast product injection devices.

GENERAL DESCRIPTION OF THE PRIOR ART

Developments in medicine have led to the development of various methods of analyzing and monitoring the status of patients. These methods include analyses carried out after injecting a contrast product, for example for medical imaging, which encompasses X-ray imaging and magnetic resonance imaging (MRI) or nuclear medicine.

There are known devices for injecting a liquid product such as a contrast product into a patient such as for example in-line pump techniques, so-called "syringe-pusher" techniques, and sachet injector techniques.

In the context of an injection, the user enters an injection protocol on a keyboard, notably by entering the injection flow rate required at the outlet from the injection device, known as the "set point flow rate".

A problem linked to the injection of liquid product using such a device concerns maintaining an outlet flow rate conforming to the set point flow rate.

The document WO 97/45150 proposes controlling an injection device as a function of a flow rate measured at the outlet of the invention device. The injection device comprises driving means for injection of the liquid product, a flow meter disposed at the outlet of the injection device, and a control unit generating a motor command to control the electrical actuation of the driving means. The control unit is connected to the flow meter to receive a signal representative of the flow rate of the liquid product leaving the injection device. The control unit varies the motor command as a function of this signal.

A disadvantage of the above device concerns on the one hand the cost of the consumables that a disposable flow meter system includes and on the other hand the poor quality of the flow rate measurement produced by the flow meter, which is insufficiently accurate.

An object of the invention is to propose a device for injection of liquid product that enables the cost of consumables to be reduced and accuracy to be improved in the evaluation of the outlet flow rate from the injector.

STATEMENT OF THE INVENTION

To this end, the invention proposes a system for injection into a patient of a liquid product contained in a container, the system comprising a pressurization unit for driving the liquid product contained in the container, remarkable in that the system further comprises a computer programmed to implement the following steps:
  receiving information representative of a real flow rate of advance of the pressurization unit,
  receiving information representative of a pressure inside the container,
  estimating an imaginary leakage flow rate as a function of a law of deformation of the injection system under the effect of the pressure inside the container,
  continuously estimating an outlet flow rate from the container corresponding to the difference between the real flow rate of advance of the pressurization unit and the imaginary leakage flow rate.

"Information representative" is understood to mean a signal obtained from a detector, for example a position encoder or a pressure sensor. Said signal can be obtained by measuring a force using a strain gauge or using a current, for example. There may be a conversion ratio applied between the value obtained through said signal and the value actually transmitted to the computer.

In the context of the present invention, "estimation" means calculation of the injection flow rate from one or more acquired instantaneous values. By "continuous estimation" is meant the repetition of this injection flow rate calculation at regular intervals during a certain time period that may be equal to the injection time period.

By "real flow rate of advance" is meant the flow rate generated by the pressurization unit as a function of a set point flow rate entered by the user.

By "imaginary leak" in a pipe is meant all physical phenomena impacting on an outlet flow rate, with the exception of losses of liquid that are considered as a real leak. These phenomena may comprise for example the compressibility of the fluid, the deformation of the pipe or backflow of the fluid in the pipe.

By "imaginary leakage flow rate" is meant a quantity of liquid per unit time equal to a difference between a flow rate imposed by an injector and a flow rate ejected from a container containing the liquid product to be injected. This flow rate is referred to as an "imaginary leakage flow rate" in that there is no loss of liquid in the injection system between the container containing the liquid product to be injected and the outlet of the injection system.

The imaginary leakage flow rate thus corresponds:
  during the injection phase (during which phase the pressurization unit exerts a force on the container to eject the liquid product from the container), to a quantity of liquid per unit time that is not ejected from the container,
  during the off phase (during which phase the pressurization unit exerts no force on the container), to a quantity of liquid per unit time that flows out of the container (residual flow out of the container in the absence of force exerted by the pressurization unit on the container).

Thus, and as described below, the invention proposes computing an imaginary leakage flow rate from a law of deformation of the injection system as a function of the pressure inside the container.

The reader will appreciate that this deformation of the system is of elastic type (i.e., this deformation is reversible), unlike a plastic deformation or a deformation with wear (i.e. a non-reversible deformation). Moreover, the reader will appreciate that, in the context of the present invention, "system" should be understood to mean the assembly composed:

of the pressurization unit and
of the container,
this assembly not comprising (i.e. being without):
either the connections for supplying liquid to the patient,
or the contrast product per se.

Thus, the law of deformation of the system takes into account the deformation of the pressurization unit and the deformation of the container.

Preferred but nonlimiting aspects of the system of the invention are as follows:
the computer estimates the imaginary leakage flow rate as a function of the pressure inside the container;
the pressurization unit is composed of at least one enclosure designed to receive a sachet containing the liquid product to be injected and comprising at least one flow orifice designed to be connected to a tube connected to the patient via an injection pipe, the enclosure including at least one variable volume membrane deformable as a result of the action of a driving fluid injected into said enclosure so as to compress the sachet in order to force the liquid product to be injected to flow in the tube;
the computer includes a self-adjusting regulator—such as a regulator of proportional-integral type—the computer automatically adjusting parameters of the regulator—such as coefficients $K_i$, $K_p$—as a function of the pressure inside the container and the set point flow rate entered by the user;
the computer is programmed to determine a reference outlet flow rate as a function of information relating to the nature of the liquid product contained in the container;
the computer is programmed:
to compare the reference outlet flow rate to the estimated outlet flow rate, and
to emit an alarm if the difference between the reference outlet flow rate and the estimated outlet flow rate is above a threshold value;
the system further comprises a display for displaying a graph representing a outlet flow rate from the container as a function of time, the outlet flow rate being equal to the difference between the set point flow rate and the estimated imaginary leakage flow rate;
the liquid product is a contrast product.

The invention further proposes a method of controlling a system of injection into a patient of a liquid product contained in a container, the method comprising a step consisting in controlling the driving of the liquid product contained in the container using a pressurization unit of the injection system, characterized in that the method comprises the following steps:
receiving information representative of a real flow rate of advance of the pressurization unit,
receiving information representative of a pressure inside the container,
estimating an imaginary leakage flow rate as a function of a law of deformation of the injection system under the effect of the pressure inside the container,
continuously estimating an outlet flow rate from the container corresponding to the difference between the real flow rate of advance of the pressurization unit and the imaginary leakage flow rate.

DESCRIPTION OF THE FIGURES

Other features and advantages of the invention will emerge from the following description, which is purely illustrative and not limiting on the invention, and must be read with reference to the appended drawings, in which:

FIG. 13 shows a deformation law, FIG. 14 show an algorithm for estimating the outlet flow rate from the device shown in FIG. 7.

DESCRIPTION OF EMBODIMENTS OF THE INVENTION

The invention will now be described in more detail with reference to the figures. In the various figures, equivalent elements bear the same reference numbers.

1. Estimation of the Outlet Flow Rate from the Injection Device

Instead of measuring the outlet flow rate from the injection device directly, the invention proposes to estimate the outlet flow rate from the injection device.

On the one hand, this enables the accuracy of the evaluation of the outlet flow rate from the injector to be improved. Most flow meters do not take into account possible variations in the mass per unit volume of the liquid product contained in the container, which is a source of error in the measurement of the outlet flow rate.

On the other hand, this enables the costs of consumables to be reduced, the flow meters used to measure the outlet flow rate from an injection device generally being disposable.

1.1. Syringe Pusher Type Device

Figure 1:
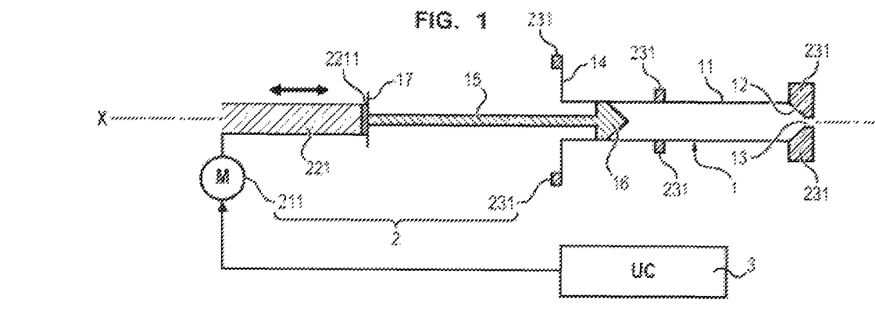
FIGS. 1 and 2 show one embodiment of an injection device.
Figure 2:
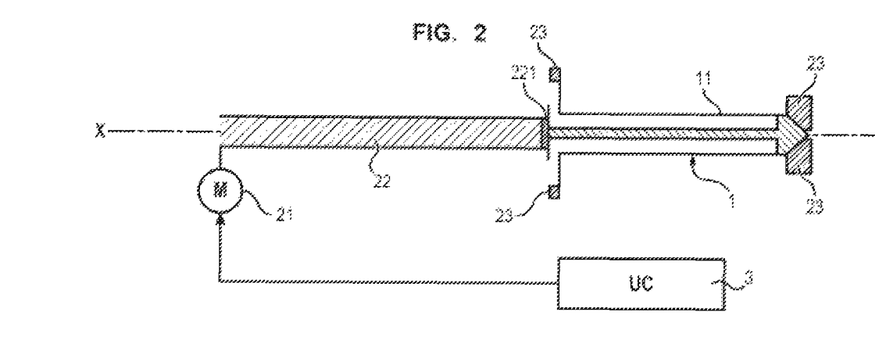

Referring to FIGS. 1 and 2, there is shown an example of a syringe-pusher type injection device. The device comprises a pressurization unit 2 and a control unit 3.

The injection device enables injection of a liquid product contained in a syringe 1.

1.1.1. Syringe

The syringe 1 comprises a cylindrical body 11 the front part 12 of which converges to an outlet pipe 13 equipped with a connector for a flexible tube (not shown). The rear end of the cylindrical body 11 is provided with a radial external flange 14 of substantially circular exterior shape.

In the context of the present invention, by "substantially circular exterior shape" is meant a truncated circular shape or an oval shape.

In the cylindrical body 11 there is disposed a piston 15. The front face of this piston is covered with an elastomer seal 16 and has a conical shape conjugate with the front part 12 of the cylindrical body 11 of the syringe 1. The seal 16 is extended rearwardly so as to rub on the interior wall of the cylindrical body 11. The rear face of the piston 15 is plane and provided at its centre with a circular section mushroom-shaped peg 17.

1.1.2. Pressurization Unit

The pressurization unit 2 comprises driving means composed of:
- a motor 211,
- a support 231 to hold the syringe in a fixed position, and
- a pusher 221 mobile in translation along an axis X-X' under the control of the control unit 3.

The motor 211 enables the pusher 221 to be moved along the axis X-X'.

The support 231 is composed of half-disks disposed along the cylindrical body 11 of the syringe 1 and is extended toward the front by a semi-cylindrical cradle designed to receive the front part of the cylindrical body. The shape of the cradle is complementary to the conical shape of the front part of the cylindrical body 11. The cradle comprises an opening for the outlet pipe 13 of the cylindrical body 11 to pass through.

The pusher 221 is of cylindrical general shape. It includes at the front a head 2211 designed to come into contact with the peg 17 of the piston 15 of the syringe 1. The pusher 221 may be moved between a deployed position (see FIG. 1) and a retracted position (see FIG. 2), the head 2211 at the front of the pusher 221 being closer to the semi-cylindrical cradle of the support 231 in the retracted position than in the deployed position.

1.1.3. Control Unit

The control unit 3 controls the pressurization unit.

To be more precise, the control unit is designed to generate an electrical control signal for the motor of the pressurization unit, notably as a function of a set point flow rate entered by the user of the injection device on input means—such as a keyboard, a touch-sensitive screen, etc.—of the injection device.

The control unit may include a computer notably enabling estimation of the outlet flow rate of the pressurization unit as will be described in more detail hereinafter.

The computer comprises for example one or more computers, processors, microcontrollers, microcomputers, programmable automatic controllers, application-specific integrated circuits, other programmable circuits or other devices that include a computer such as a workstation.

The control unit may be integrated into the pressurization unit or separate from the pressurization unit.

The computer is coupled to one or more memories that may be integrated into or separate from the computer. The memory may be a ROM/RAM, a USB key, a memory of a central server. This memory may enable storage of the flow rates estimated by the computer or other data used by the computer.

1.1.4. Example of a Method of Estimation by the Computer of the Outlet Flow Rate

1.1.4.1. Pressure Measurement

To estimate the outlet flow rate from the injection device, the computer may use as information a measurement of the pressure inside the syringe. This pressure measurement may be obtained in different ways.

For example, a pressure sensor may be provided inside the syringe.

Alternatively, the injection device may comprise a strain gauge 2212 for measuring the force applied by the pressurization unit to the piston of the syringe. This strain gauge 2212 may be positioned between the head 2211 at the front of the pusher 221 and the peg 17 of the piston 15 of the syringe 1. Knowing the area S of the front face of the piston 15, and the force F exerted by the pusher 221 on the piston 15 being perpendicular to this area S, the pressure p is obtained from the following formula:

$$p = \frac{F}{S}$$

where:
- p is the pressure inside the syringe (as deduced by the computer),
- F is the force applied by the pusher to the piston of the syringe (as measured by the strain gauge), and
- S is the area of the front face of the piston (constant value: the size of the syringe is determined by the cradle).

1.1.4.2. Deformation Law Theory

The computer may advantageously also use a law of deformation of the injection device to estimate the outlet flow rate from the device.

A deformation law aims notably to model by means of empirical laws the behaviour of solids on deformation thereof.

This deformation law enables an imaginary leakage flow rate to be taken into account in the calculation of the outlet flow rate from the injection device. The leakage flow rate principle may be explained in the following terms.

The injection flow rate that is displayed on some existing injection devices is neither a measured value nor an estimate of the outlet flow rate of the injector. This displayed flow rate is based on the speed at which the pusher moves forward. In the stable state (i.e. under nominal or established conditions), the indication corresponds to the real flow rate. On the other hand, during transient states, the instantaneous outlet flow rate from the injector remains unknown.

The flows are not perfect: there are numerous sources of friction in the tubes. The friction is a function of the viscosity of the injected liquid product, the injection flow rate, the characteristics (roughness, inside diameter, etc.) of the tubes and the catheters. This friction, referred to as head loss, is reflected in a rise in pressure inside the container containing the liquid product to be injected. The injection device is deformed by the effect of this pressure. During the rise in pressure (transient conditions), part of the volume displaced by the piston is "lost" in the container deformed in this way (i.e. is not expelled to the outlet of the piston). A difference between the flow rate imposed by the pusher ($Q_{actuator}$) and the flow rate ejected from the container containing the liquid product to be injected ($Q_{injection}$) is created during this transient phase. This flow rate difference is then considered as an imaginary leakage ($Q_{leakage}$).

The following equation then applies:

$$Q_{injection}(t) = Q_{actuator}(t) - Q_{leakage}(t) \text{ where}$$

$$Q_{actuator}(t) = \frac{\omega(t)}{60} \times z \times S_{actuator} = \lambda \times \omega(t)$$

where:
- $Q_{injection}$ is the flow rate of liquid product really leaving the container containing the liquid product to be injected,
- $Q_{actuator}$ is the flow rate imposed by the pusher,
- $Q_{leakage}$ is the imaginary leakage flow rate,
- $\lambda$ is the conversion ratio in ml per revolution,
- $\omega(t)$ is the motor speed in rpm,
- $S_{actuator}$ is the section of the pusher in $mm^2$,
- z is the transmission ratio in mm/revolution.

As soon as the pressure reaches established conditions, i.e. the flow rate imposed by the pusher is equal to the outlet flow rate from the syringe, then $Q_{leakage}=0$ and $Q_{injection}(t)=Q_{actuator}(t)$.

The deformation law cited above enables the imaginary leakage flow rate to be calculated as a function of the pressure in the syringe. It is thus possible, knowing the flow rate imposed by the pusher, to estimate the injection flow rate at the outlet of the container containing the liquid product to be injected.

The deformation being a function of pressure, a characterization process enables this law of deformation as a function of pressure to be established.

Two examples of methods for determining the deformation law will now be described.

1.1.4.3. Determination of the Deformation Law

It is thanks to knowing the deformation (compliance) law of the injection device that it is possible to calculate the volume lost in deformation (called the leakage volume $V_{leakage}$) in order to proceed to estimating the injection flow rate.

The following two methods may be used to determine it.

Empirical method: This consists in progressively increasing the pressure in a closed container, filled if necessary with an incompressible liquid, and noting the pressure corresponding to the deformation volume obtained. The resulting curve may then be approximated to obtain a function that will be known to the injection device.

Theoretical method: For containers of simple geometry it is possible to obtain a theoretical law. However, the advantage of the empirical method is that it takes into account phenomena that are complex to model by mathematical equations such as the presence of mechanical clearances at low pressure and other non-linearities.

1.2. Sachet Injector

A drawback of using a syringe-pusher type injection device as described above is that it is necessary to calculate the deformation law for the different types of syringes usable in the device. In the case of a syringe-pusher type injection device, the deformation law takes into account not only the deformation of the injection device but also the deformation of the syringe itself. Now this deformation of the syringe varies from one syringe to another, notably as a function of its dimensions, the material of which it is constituted, etc.

Using a sachet injector type device enables this drawback to be alleviated. In the case of a sachet injector type injector, the container (i.e. the sachet) is not deformed by the effect of the pressure: only the injection device itself is deformed as a function of the pressure. The deformation law therefore takes account only of the deformation of the injection device.

It is therefore necessary to determine only one deformation law in the case of a sachet injector type injector, and that law is valid regardless of the characteristics (dimensions, material, etc.) of the sachet used.

Figure 7:
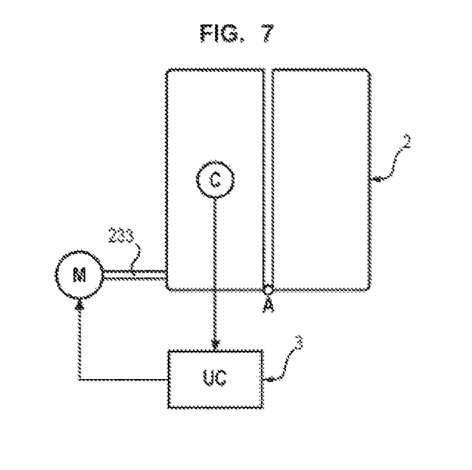
FIG. 7 shows a second embodiment of an injection device.

Referring to FIG. 7, there is shown an example of a sachet injector type injection device. The device comprises a pressurization unit 2 and a control unit 3.

Figure 3:
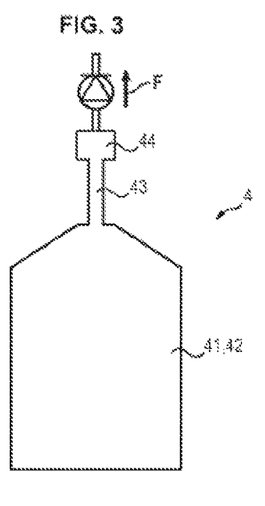
FIGS. 3 and 4 show two examples of sachets containing an injectable liquid product.
Figure 4:
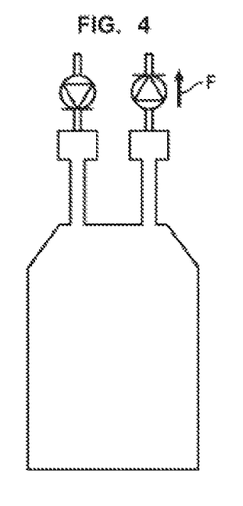

The injection device enables injection of a liquid product contained in a sachet 4 (see FIGS. 3 and 4).

1.2.1. Sachet

Referring to FIGS. 3 and 4, the medical sachet 4 includes two superposed foils 41, 42 of appropriate length and width and one or more access member(s) 43.

The foils 41, 42 are produced from a plurality of layers of thin laminated films of flexible and possibly transparent or translucent materials, such as polymer materials comprising polyethylene, polypropylene, and preferably thermoplastic materials.

The superposed foils 41, 42 are preferably flat-welded together in order to form a sachet 4, which has a zero volume before it is filled with the liquid product to be injected. The superposed foils 41, 42 are sealed at their lateral peripheries to form a sachet 4 of rectangular general exterior appearance. When the medical sachet 4 is filled or partially filled it has the shape of a cushion.

An access member 43 is provided at the level of the upper part of the sachet 4. The access member 43 is sealed between the superposed foils 41, 42. This access member 43 is a tube and may comprise at its distal end a connector 44 for coupling the sachet to a tube connected to the patient.

Another access member 43 may be provided on the sachet. In this case:
- the first access member—called the upstream access member—is designed to be connected to a source containing the liquid product to be injected into the patient to enable filling of the sachet,
- the second access member—called the downstream access member—is designed to be connected to a tube connected to the patient (via a plurality of elements such as a pipe and a catheter or a hypodermic/intravenous needle) for the injection into the patient of the liquid product.

A threshold check valve may advantageously be placed between the downstream access member and the tube connected to the patient. The threshold check valve is adapted to allow the passage of the liquid in the upstream to downstream direction as represented by the arrow "F" when a particular pressure of the flowing fluid is reached, while it blocks the passage of the medical liquid in the opposite direction, namely the downstream to upstream direction, i.e. the direction opposite that indicated by the arrow "F".

Another check valve may be placed between the upstream access member and the source to allow the passage of liquid product only from the source to the sachet.

If the sachet comprises only one access member 43, then the access member has both functions referred to above, namely filling and injection.

1.2.2. Pressurization Unit 1.2.2.1. Half-Shells

The pressurization unit 2 comprises a rigid enclosure composed of two half-shells 21, 22 articulated about a rotation axis A-A' so as to enable relative movement of the half-shells one relative to the other. These two half-shells 21, 22 are adapted to be moved relatively one relative to the other between:
- an open position (FIG. 6) for putting the sachet in place, and
- a closed position (FIG. 5) for injection of the liquid product contained in the sachet.

Figure 5:
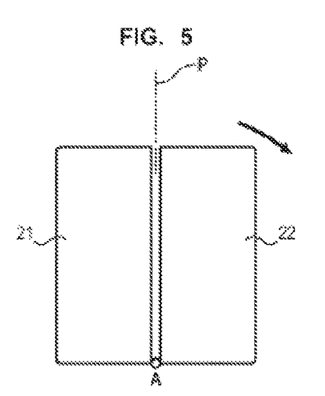
FIGS. 5 and 6 show the closed and open positions of one embodiment of a pressurization unit.
Figure 6:
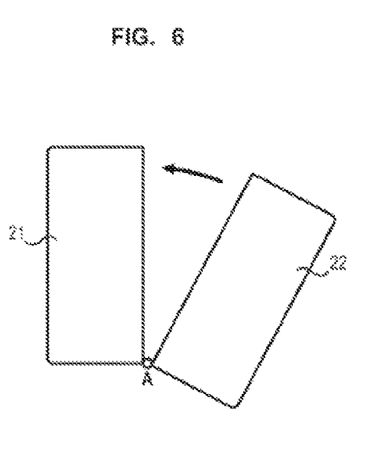

It is preferable for one of the half-shells 21 to be fixed and the other one 22 to be mobile in rotation about the axis A-A'.

The rotation axis A-A' may advantageously be offset relative to a closure plane P passing through the areas of contact between the two half-shells 21, 22 when they are in the closed position. This enables automatic opening of the mobile half-shell 22 by gravity in order to limit the number of manipulations needed by the user.

The half-shells 21, 22 are preferably not motorized in order to avoid the risks of pinching the user. Springs (not shown) may be provided between the two half-shells to assist the user to close the mobile door by compensating the weight of the mobile half-shell.

Each half-shell includes a cavity so as to form a cradle.

Figure 8:
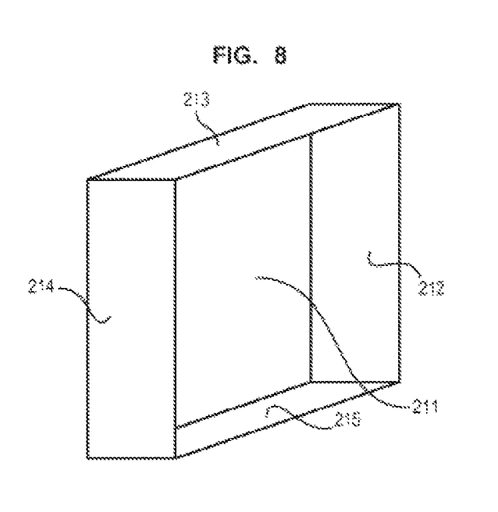
FIG. 8 shows an example of a half-shell of the device shown in FIG. 7, FIGS. 9 and 10 show a bladder of the device shown in FIG. 7, FIGS. 11 and 12 show a cushion of the device shown in FIG. 7.

In the embodiment shown in FIG. 8, each half-shell 21, 22 has a rear wall 211, a front wall and four lateral walls 212 to 215 at the periphery of the rear wall 211 and perpendicular thereto. The front wall is designed to come into contact with a sachet. The front wall may have a concave shape so as to define the cavity forming the cradle. Alternatively, one half-shell or each half-shell may be in one piece and include a single concave wall defining the cavity forming the cradle.

Figure 9:
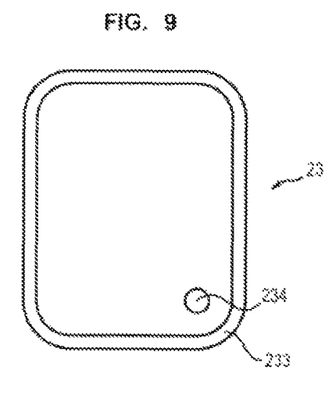
Figure 10:
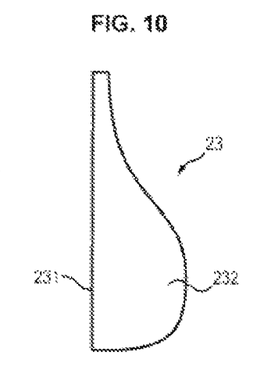

The cavity of one of the half-shells—for example the fixed half-shell 21—is designed to receive a bladder 23 shown in FIGS. 9 and 10. The bladder 23 is composed of at least two membranes 231, 232 welded at their periphery. These welded membranes 231, 232 form a space designed to receive a drive fluid causing a variation in the volume of the bladder 23 in order to induce a deformation thereof. The bladder 23 is fed with drive fluid by means of a hydraulic actuator M connected to the bladder 23 via hydraulic feed hoses 233.

Figure 11:
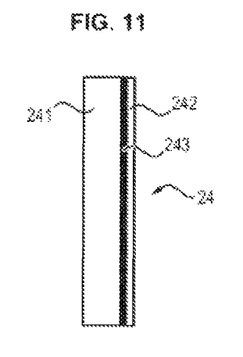
Figure 12:
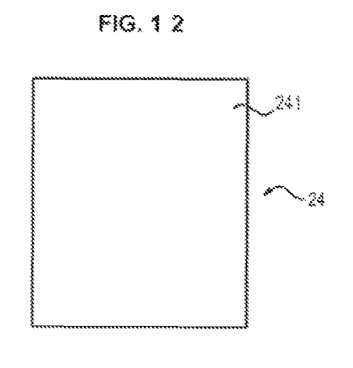

The cavity of the other half-shell—for example the half-shell 22 mobile in rotation—is designed to receive a deformable damper cushion 24 of constant volume. This cushion 24 is called a "passive cushion" in that it is not fed with drive fluid. Its deformation is related to the forces applied to it. The fact that the mobile half-shell 22 is adapted to receive a passive cushion 24 enables the presence of a hydraulic supply (for the drive fluid) on the mobile half-shell to be avoided. This enables the overall size of the injection device to be small because it is not necessary to provide clearance so that hydraulic feed hoses 233 can move with the mobile half-shell 22. This also enables manipulation of the injection device to be facilitated since it is no longer necessary for the user to assist the movement of the hydraulic feed hoses.

The half-shells 21, 22 may be made of aluminium, for example, or a glass fibre or carbon fibre composite material.

The half-shells 21, 22 may advantageously open in two positions:
- a first or preparation position in which the two half-shells are at an angle from 10° to 45° relative to one another; this first open position enables insertion of a sachet into the injection device,
- a second or maintenance position in which the two half-shells are at an angle from 85° to 95° relative one another, preferably 90°; this second open position enables cleaning of the injection device.

1.2.2.2 Bladder

One membrane 232 of the bladder 23—called the "back membrane"—is designed to face the rear wall 211 of the half-shell.

The shape of the back membrane 232 is preferably complementary to the shape of the rear wall 211 of the half-shell. For example, in one embodiment, the back membrane 232 and the rear wall 211 are in the shape of a droplet (see FIG. 10). This enables the quantity of drive fluid to be introduced into (respectively extracted from) the bladder 23 to increase (respectively decrease) its volume to be limited. This limits the overall size of the injection device and improves the responsiveness of the device at a given filling speed.

The other membrane 231—called the front membrane—is designed to face the sachet 4.

The stiffness of the back membrane 232 may be made greater than the stiffness of the front membrane 231. For example,
- the front membrane 231 may be flexible and have a Shore A hardness of the order of 30 to 40,
- the back membrane 232 may be semi-rigid and have a Shore A hardness of the order of 80.

The fact that the back membrane 232 has a greater stiffness than the front membrane 231 enables:

- on the one hand good placement of the back membrane 232 against the rear wall 211 of the half-shell even at low pressure,
- on the other hand a guarantee that, on introduction of the drive fluid into the bladder 23, it is the front wall 231 of the bladder 23 that is deformed.

The bladder 23 also comprises an opening 234—for example in the back membrane 232—for the drive fluid to pass through. Introduction of the drive fluid into (respectively withdrawal of the drive fluid from) the bladder 23 induces a variation (increase or decrease) in its volume that causes its deformation.

Finally, the bladder 23 comprises an annular and rigid reinforcing body 233. This reinforcing body 233 lies at the periphery of the membranes of the bladder 23. This reinforcing body 233 is made of metal or Dacron, for example. The presence of a reinforcing body 233 at the periphery of the membranes of the bladder 23 enables prevention of the formation of a hernia (i.e. a bead) between the half-shells 21, 22 during introduction of driving fluid into the bladder when the half-shells are in the closed position.

1.2.2.3. Cushion

According to FIGS. 11 and 12, the passive cushion 24 comprises a thick flexible layer 241. This thick layer 241 is preferably constituted in a material of zero Shore A hardness and possibly of high thermal conductivity.

The material constituting the thick layer 241 is silicone or polyurethane, for example.

If the thick layer 241 is a silicone layer, it may be covered with a thin non-stick layer to limit friction between the sachet and the passive cushion 24. This thin layer is for example a layer of polyurethane paint or a cotton or Lycra® covering.

The passive cushion 24 may comprise a rigid rear face 242 designed to face the rear wall 211 of the half-shell. In this case, the rigid rear face 242 has a shape conjugate with the shape of the rear wall 211 of the half-shell. The presence of a rigid rear face 242 on the cushion 24 facilitates its manipulation.

The passive cushion 24 may equally comprise one or more heating element(s) 243 composed for example of an insulative layer and a resistive layer, or any other type of heating element known to the person skilled in the art. The presence of a heating element 243 enables the liquid product contained in the sachet to be maintained at a required temperature prior to its injection into the patient.

The heating element 243 is preferably positioned between the rigid rear face 242 and the thick flexible layer 241. It is preferable to position the heating element between the rear face and the thick layer to limit the risk of deterioration of the latter because:
- the heating element is not extendable, and
- the thick layer is intended to be deformed.

1.2.2.4. Sachet End Piece Housing

The injection device may also comprise a sachet end piece housing on one of the half-shells 21, 22. This housing is designed to receive the connector for connecting the access member 43 of the sachet 4 or any type of coupling element positioned at the distal end of the access member 43.

The shape of this housing preferably has symmetry of revolution. This enables correct positioning of the sachet in the pressurization unit to be obtained by gravity without requiring particular attention on the part of the user. The housing has a frustoconical shape (like a funnel), for example, or a cylinder shape.

The housing also has a longitudinal slot on its internal face. This slot is designed to receive the end of a tube coupled to the access member. This enables correct positioning of the tube along the injection device to be achieved.

A bubble sensor may be provided at the level of this longitudinal slot to enable detection of bubbles in the tube connected to the patient.

1.2.3. Control Unit

The control unit comprises the same elements as in the syringe-pusher embodiment, notably a computer. These elements will not be described again here.

1.2.3.1. Estimation of the Outlet Flow Rate from the Injector

The hydraulic compression technology enables continuous injection without pulsation of all of the injectable liquid product contained in the sachet. When the sachet of injectable liquid product is pressed against the front membrane of the bladder and the thick layer of the cushion, any relative movement of driving fluid by the hydraulic actuator toward the rigid enclosure induces the same movement of the injectable liquid product. This is the principle of conservation of flow rate. Accordingly, injection of 80 ml of injectable liquid product at 3 ml/s will be obtained by introduction of 80 ml of incompressible driving fluid at a flow rate of 3 ml/s.

However, there exists no perfectly incompressible fluid and no undeformable material. Compensation is therefore necessary to accelerate these phenomena and reach established conditions quickly.

Moreover, in the real world, the flows are not perfect: there are numerous sources of friction in the tubes. This friction is a function of the viscosity of the injectable liquid products, the injection flow rate, the characteristics (roughness, inside diameter, etc.) of the tubes and the catheters. This friction, referred to as "head loss", is reflected by an increase in pressure in the rigid enclosure. The enclosure is liable to be deformed by the effect of the pressure, thus creating, throughout the pressure rise time period (transient conditions), an imaginary leakage flow rate between the flow rate imposed by the hydraulic actuator and the flow rate of liquid product actually ejected from the sachet.

The following equation then applies:

$$Q_{injection}(t) = Q_{actuator}(t) - Q_{leakage}(t) \text{ where}$$

$$Q_{actuator}(t) = \frac{\omega(t)}{60} \times z \times S_{actuator} = \lambda \times \omega(t)$$

where:

$Q_{injection}$ is the flow rate of liquid product really leaving the device, $Q_{actuator}$ is the flow rate imposed by the hydraulic actuator, $Q_{leakage}$ is the imaginary leakage flow rate, $\lambda$ is the conversion ratio in ml per revolution, $\omega(t)$ is the speed in rpm of the motor driving the hydraulic actuator, $S_{actuator}$ is the section of the hydraulic actuator in $mm^2$ z is the transmission ratio in mm/revolution.

As soon as the pressure reaches established conditions, i.e. the flow rate at the outlet of the hydraulic actuator is equal to the outlet flow rate from the sachet, then $Q_{leakage}=0$ and $Q_{injection}(t)=Q_{actuator}(t)$.

$Q_{leakage}$ is the derivative with respect to the time of the deformation volume $V_{leakage}$ of the enclosure.

This deformation law is itself a function of pressure. As described above, a characterization process enables this deformation law as a function of pressure to be established. There is then obtained:

$$V_{leakage} = f(p)$$

Figure 13:
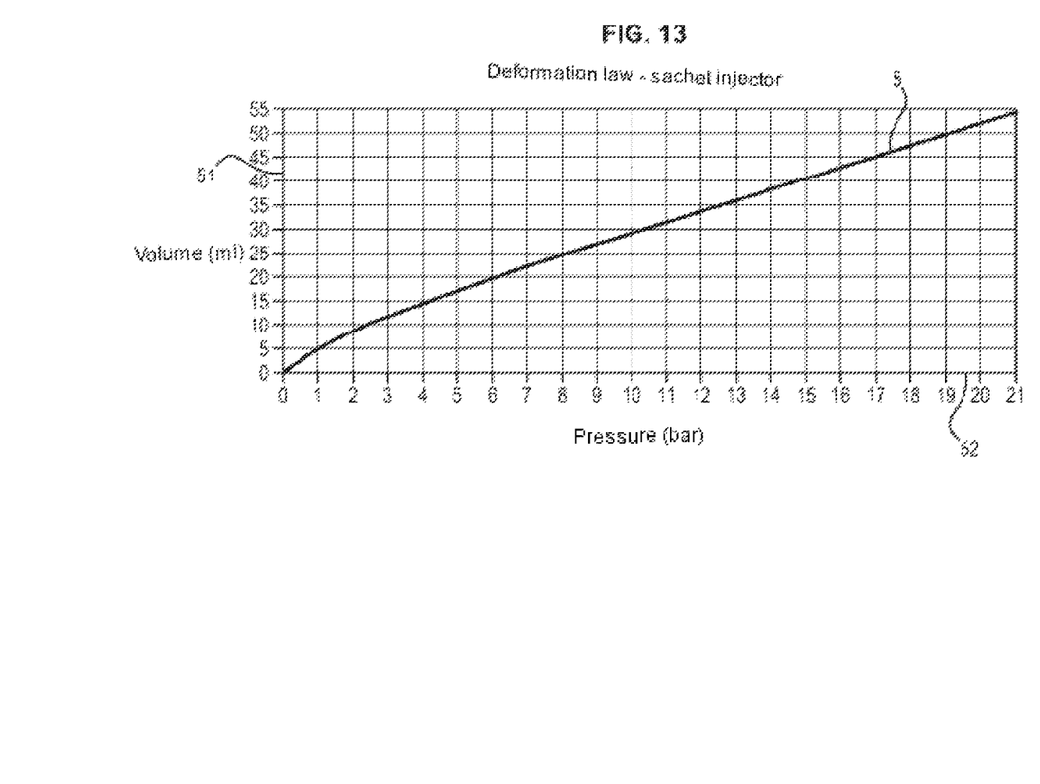

Referring to FIG. 13, there is shown an example of a deformation law 5 enabling determination of a leakage volume 51 as a function of the pressure in the enclosure 52. The pressure in the enclosure may be measured by providing a pressure sensor C in the bladder 23, for example.

Thus $Q_{injection}(t)$ can be calculated in real time to control the advance of the hydraulic actuator.

2. Control of the Pressurization Unit as a Function of the Outlet Flow Rate

The pressurization unit may be controlled in a similar manner for both embodiments (i.e. syringe-pusher and sachet injector) described above.

The principle of controlling the pressurization unit will be described hereinafter with reference to the sachet injector type embodiment, it being understood that this principle may be transposed to the syringe-pusher type injection device.

When the enclosure is pressurized, it tends to become deformed. This deformation is not instantaneous and lasts until the injection pressure has reached its final value. This is what is meant by reference to established conditions.

If the injection device is not controlled the stabilization time is much too long to be able to guarantee that the volume injected and the duration of injection remain within tolerances acceptable to the user.

It is thus possible to regulate the outlet flow rate from the injection device by operating on the control input to the actuator.

This regulation or control may use a PI (Proportional Integral) type regulator—referred to hereinafter as a "PI regulator"—to accelerate the rise in pressure at the same time as complying with a minimum overshoot of the set point flow rate entered by the user.

The parameters of the regulator being adapted to only one configuration of the injection device, one set of parameters is not sufficient to be able to cover all ranges of flow rate and configurations of the injection device (i.e. type of injectable liquid product, tubes connected to the patient, catheters, etc.).

One method enabling the provision of a PI regulator that is self-adjusting as a function of the injection context has been developed on the basis of functions that define the parameters to be used as a function of:

the instantaneous pressure in the container containing the injectable liquid product, and the set point flow rate entered by the user on input means (such as a keyboard, a touch-sensitive screen, etc.) of the injection device.

These functions are represented in the table set forth below. As a function of a set point flow rate and a pressure in the container 4, it is possible determine:

a proportional term "Kp" from the proportional function, and an integral term "Ki" from the integral function.

As may be seen from the proportional and integration functions, the higher the pressure in the enclosure rises, the greater the proportional term Kp must be to compensate the rapid deformation of the enclosure. On the other hand, this term is decremented for injection at a high flow rate. For the integral term Ki, note the pressure of a plateau at high pressure and a high flow rate, which prevents an excessive cumulative error during a very slow rise in pressure in the enclosure. The integral term Ki decreases exponentially as a function of pressure and retains a low value at high flow rates, even if the pressure is high.

Curves of Ki and Kp can be obtained by manual calibration of the PI regulator on the physical system with the standard adjustment ("tuning") methods.

The table below gives examples of values for the integral term Ki and the proportional term Kp for different values of set point flow rate and pressure measured inside the container.

|  |  | Pressure (bar) | | | | | | | | | | |
| --- | --- | --- | --- | --- | --- | --- | --- | --- | --- | --- | --- | --- |
|  |  | 0 | 2 | 4 | 6 | 8 | 10 | 12 | 14 | 16 | 18 | 20 |
| Ki | | | | | | | | | | | | |
| Flow rate (ml/s) | 0 | 2.53 | 0.994 | 0.729 | 0.698 | 0.692 | 0.691 | 0.691 | 0.692 | 0.693 | 0.693 | 0.694 |
| | 2 | 2.53 | 1.465 | 0.798 | 0.72 | 0.7 | 0.694 | 0.691 | 0.691 | 0.691 | 0.691 | 0.692 |
| | 4 | 2.53 | 2.53 | 0.968 | 0.777 | 0.725 | 0.706 | 0.697 | 0.693 | 0.692 | 0.691 | 0.691 |
| | 6 | 2.53 | 2.53 | 1.399 | 0.916 | 0.789 | 0.74 | 0.717 | 0.705 | 0.699 | 0.695 | 0.693 |
| | 8 | 2.53 | 2.53 | 2.53 | 1.263 | 0.945 | 0.825 | 0.769 | 0.739 | 0.721 | 0.711 | 0.704 |
| | 10 | 2.53 | 2.53 | 2.53 | 2.208 | 1.339 | 1.035 | 0.897 | 0.823 | 0.78 | 0.753 | 0.735 |
| Kp | | | | | | | | | | | | |
| Flow rate (ml/s) | 0 | 1.202 | 1.722 | 4.252 | 6.752 | 8.893 | 10.911 | 12.947 | 15.035 | 17.158 | 19.284 | 21.384 |
| | 2 | 1.202 | 1.332 | 2.725 | 4.667 | 6.458 | 8.045 | 9.521 | 10.966 | 12.424 | 13.909 | 15.42 |
| | 4 | 1.202 | 1.221 | 1.781 | 3.019 | 4.423 | 5.754 | 6.967 | 8.087 | 9.151 | 10.191 | 11.229 |
| | 6 | 1.202 | 1.203 | 1.353 | 1.943 | 2.844 | 3.85 | 4.846 | 5.788 | 6.668 | 7.495 | 8.283 |
| | 8 | 1.202 | 1.202 | 1.225 | 1.414 | 1.845 | 2.453 | 3.151 | 3.878 | 4.597 | 5.291 | 5.953 |
| | 10 | 1.202 | 1.202 | 1.204 | 1.239 | 1.376 | 1.642 | 2.019 | 2.471 | 2.969 | 3.487 | 4.01 |

The operating principle of the injection device of the invention will now be described with reference to FIGS. 14 and 15.

The user unlocks the pumping means of the device. The mobile half-shell rotates about the rotation axis A-A' to the open position (FIG. 6) for fitting the sachet 4. The user inserts the access member 43 into the longitudinal slot of the end piece housing, the connector being at the top and the sachet at the bottom. Because of the symmetry of revolution of the end piece housing, the sachet is positioned correctly between the two half-shells by the effect of gravity.

The user then closes the enclosure by moving the mobile half-shell into a vertical position. When the two half-shells are in contact, locking means are actuated either automatically or manually.

The control unit commands movement of the hydraulic actuator to inflate the bladder of the fixed half-shell to ensure correct placement of the bladder and the passive cushion against the faces of the sachet 4. Because of the presence of the threshold valve at the outlet of the injection device, no injectable liquid product is expelled from the sachet before the faces of the sachet are pressed against the bladder on the one hand and the cushion on the other hand.

The user then enters injection parameters, notably a set point flow rate, on a touch-sensitive screen of the injection device. This set point flow rate is received by the control unit, which starts the injection protocol.

Figure 15:
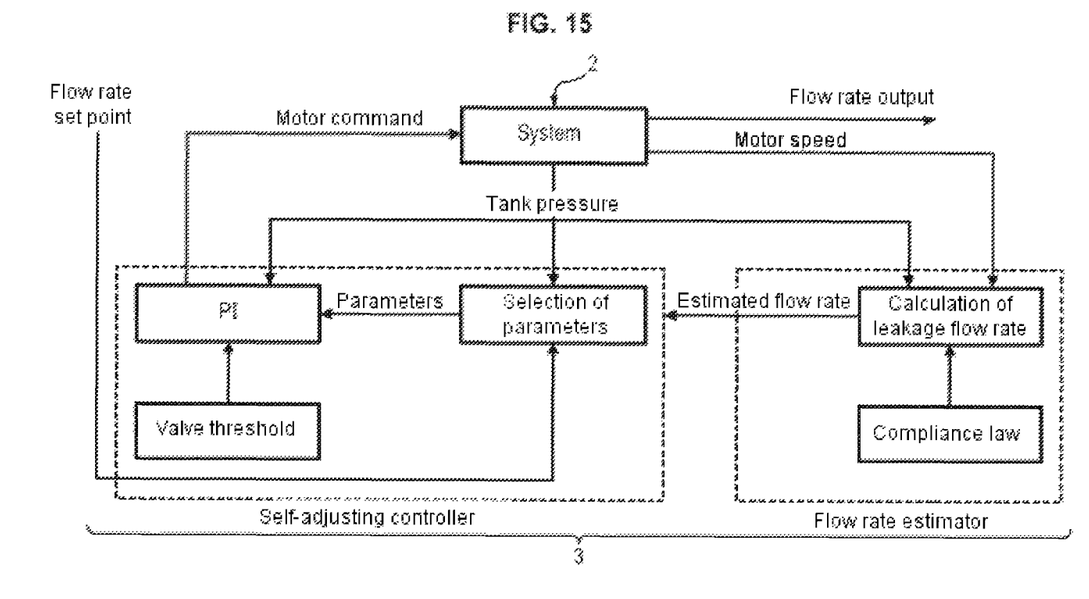
FIG. 15 is a block diagram of the device shown in FIG. 7.

The computer receives in real time the pressure measured by the pressure sensor placed in the bladder, as shown in FIG. 15 (step 61). The computer also receives a driving flow rate corresponding to the driving fluid flow rate displaced by the hydraulic actuator and measured using any technique known to the person skilled in the art.

The computer compares the measured pressure to the pressure at which the threshold valve opens (step 62). If this measured pressure is less than the opening pressure, then the outlet flow rate is nil (step 63).

Otherwise, the computer estimates the leakage volume (or enclosure deformation volume) from the measured pressure and the deformation function (step 64). The computer then differentiates this calculated leakage volume with respect to time to obtain the imaginary leakage flow rate of the device (step 65).

This imaginary leakage flow rate is then subtracted from the measured driving flow rate to obtain the estimated injection flow rate at the outlet of the enclosure (step 66).

This estimated injection flow rate will be used by the computer to compare it with the set point flow rate. The difference between these two flow rates constitutes the error to be corrected by the computer by means of the PI regulator.

The computer determines the regulation parameters Ki and Kp from the set point flow rate, the measured pressure in the enclosure and the proportional and integral curves.

The computer converts the parameters Ki and Kp and the error to be corrected into a motor command by means of the PI regulator.

3. Other Control Unit Functions

In addition to estimating the outlet flow rate and controlling the injection device, the control unit enables verification of the consistency of the nature of the liquid product contained in the pressurization unit and the information entered by the user.

The nature of the liquid product present in the sachet may be determined by an analysis of its behaviour in the enclosure. The rise in pressure of the enclosure is different according to the viscosity of the liquid driven in the tubes.

For example, a liquid product of contrast product type will have a more progressive rise in pressure than a liquid product of physiological serum type. If there is a behaviour difference between the expected behaviour of the liquid product the nature of which has been entered by the user and the behaviour of the liquid product actually present in the enclosure, then the manipulation error can be detected.

The control unit can therefore be programmed:
- to receive information as to the nature of the liquid product contained in the sachet, this information being entered by the user on the input means of the injection device,
- to estimate the outlet flow rate from the injection device,
- to compare the expected outlet flow rate to the estimated outlet flow rate,
- to emit an alarm if the difference between the estimated outlet flow rate and the reference outlet flow rate is above a threshold.

The reader will have understood that numerous modifications may be made without departing materially from the new teachings and advantages described here.

For example, in the case of a sachet injector type pressurization unit, the injection device may comprise two pairs of half-shells enabling successive or simultaneous injection of different injectable liquid products.

Consequently, all modifications of this type are intended to be incorporated within the scope of the appended claims.

The invention claimed is:

1. An injection system comprising:
an injection device comprising:
a pressurization unit comprising a first enclosure section and a second enclosure section, wherein the pressurization unit is movable between an open position and a closed position, wherein the pressurization unit further comprises a variable volume bladder, and
a hydraulic actuator fluidly connected with the bladder,
a container disposed between the first and second enclosure sections when the pressurization unit is in the closed position and that is engageable by the bladder, wherein the container has a liquid product, wherein inflation of the bladder by drive fluid from movement of the hydraulic actuator compresses the container to discharge the liquid product out of the container for injection into a patient, and
a computer programmed to implement the following steps:
receiving information representative of a real flow rate of advancement of the hydraulic actuator of the pressurization unit,
receiving information representative of a pressure inside the container containing the liquid product,
estimating an imaginary leakage flow rate of the liquid product as a function of a law of deformation of the injection device under the effect of the pressure inside the container containing the liquid product, wherein during an injection the imaginary leakage flow rate corresponds to a quantity of liquid per unit time that is not elected from the container,
continuously generating an estimated outlet flow rate of the liquid product being discharged from the container corresponding to the difference between the real flow rate of advancement of the hydraulic actuator of the pressurization unit and the imaginary leakage flow rate of the liquid product.

2. Injection system according to claim 1, wherein the computer estimates the imaginary leakage flow rate as a function of the pressure inside the container.

3. Injection system according to claim 1, wherein the law of deformation accounts only for the deformation of the infection device and not the container.

4. Injection system according to claim 1, wherein the computer comprises a self-adjusting regulator that is of a proportional-integral type, wherein the computer automatically adjusts each of a proportional term constant and an integral term constant of the self-adjusting regulator that are each a function of the pressure inside the container and a set point flow rate entered by a user.

5. Injection system according to claim 1, wherein the computer is programmed to determine a reference outlet flow rate as a function of information relating to the nature of the liquid product contained in the container.

6. Injection system according to claim 5, wherein the computer is programmed:
to compare the reference outlet flow rate to the estimated outlet flow rate, and
to emit an alarm if the difference between the reference outlet flow rate and the estimated outlet flow rate is above a threshold value.

7. Injection system according to claim 1, wherein the liquid product is a contrast product.

8. Injection system according to claim 1, wherein the first enclosure section comprises the bladder, wherein the second enclosure section comprises a deformable damper cushion, and wherein the container is located between the bladder and the damper cushion when the pressurization unit is in the closed position.

9. Injection system according to claim 8, wherein the bladder comprises first and second membranes that are oppositely disposed, wherein the first membrane engages a rear wall of the first enclosure section, wherein the second membrane engages the container, wherein both the first membrane and the second membrane are located between the container and the rear wall of the first enclosure section when the pressurization unit is in the closed position, and wherein a stiffness of the first membrane is greater than a stiffness of the second membrane.

10. Injection system according to claim 8, wherein the damper cushion is of a passive configuration.

11. Injection system according to claim 8, wherein the damper cushion comprises a flexible layer that engages the container when the pressurization unit is in the closed position, along with a rigid rear face that engages a rear wall of the second enclosure section such that the flexible layer is located between the container and the rigid rear face when the pressurization unit is in the closed position.

12. Injection system according to claim 8, wherein the damper cushion comprises at least one heating element.

13. Injection system according to claim 1, wherein the first enclosure section comprises a first cavity in which the bladder is positioned, wherein the bladder comprises first and second membranes that are oppositely disposed, wherein the first membrane engages a rear wall of the first enclosure section, wherein the second membrane engages the container, wherein both the first membrane and the second membrane are located between the container and the rear wall of the first enclosure section when the pressurization unit is in the closed position, and wherein a stiffness of the first membrane is greater than a stiffness of the second membrane.

14. Injection system according to claim 1, wherein the second enclosure section comprises a second cavity in which a damper cushion is received.

15. Injection system according to claim 14, wherein the damper cushion is of a passive configuration.

16. Injection system according to claim 14, wherein the damper cushion comprises a flexible layer that engages the container when the pressurization unit is in the closed position, along with a rigid rear face that engages a rear wall of the second enclosure section such that the flexible layer is located between the container and the rigid rear face when the pressurization unit is in the closed position.

17. Injection system according to claim 14, wherein the damper cushion comprises at least one heating element.

18. Injection system according to claim 1, further comprising a control unit operatively interconnected with the hydraulic actuator and comprising a proportional-integral regulator, wherein the computer determines both a proportional term constant and an integral term constant from a pressure inside the container and a set point flow rate entered by a user.

19. Injection system according to claim 1, wherein the computer is configured to compare the estimated outlet flow rate with a set point flow rate for flow out of the container.

20. Injection system according to claim 19, wherein a difference between the estimated outlet flow rate and the set point flow rate constitutes an error that is used by a proportional-integral regulator to control operation of the hydraulic actuator.

* * * * *

UNITED STATES PATENT AND TRADEMARK OFFICE
CERTIFICATE OF CORRECTION

PATENT NO. : 9,662,439 B2
APPLICATION NO. : 14/406681
DATED : May 30, 2017
INVENTOR(S) : Rebergue et al.

Page 1 of 1

It is certified that error appears in the above-identified patent and that said Letters Patent is hereby corrected as shown below:

In the Specification

Figure 14:
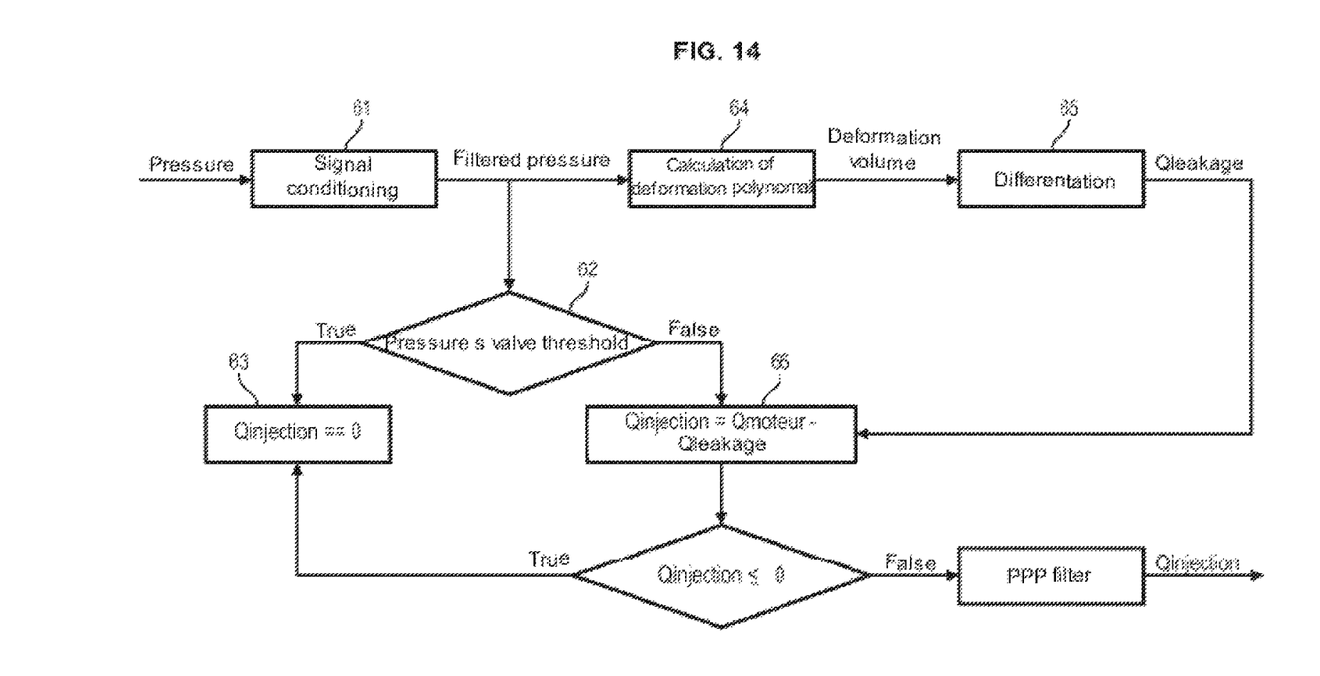

Column 4, Line 19, delete "FIG. 14 show" and insert therefore --FIG. 14 shows--

In the Claims

Column 15, Line 40 (Line 31 of Claim 1), delete "elected" and insert therefore --ejected--

Column 15, Line 52 (Line 3 of Claim 3), delete "infection" and insert therefore --injection--

Signed and Sealed this
Fifteenth Day of May, 2018

Andrei Iancu
*Director of the United States Patent and Trademark Office*